United States Patent [19]

Casey et al.

[11] 4,076,798
[45] Feb. 28, 1978

[54] HIGH MOLECULAR WEIGHT POLYESTER RESIN, THE METHOD OF MAKING THE SAME AND THE USE THEREOF AS A PHARMACEUTICAL COMPOSITION

[75] Inventors: Donald J. Casey, Ridgefield; George C. Gleckler, Stamford, both of Conn.

[73] Assignee: American Cyanamid Company, Stamford, Conn.

[21] Appl. No.: 737,940

[22] Filed: Nov. 2, 1976

Related U.S. Application Data

[62] Division of Ser. No. 582,001, May 29, 1975, which is a division of Ser. No. 418,138, Nov. 21, 1973, abandoned.

[51] Int. Cl.$^2$ ............................................. A61K 47/00
[52] U.S. Cl. ..................................... 424/22; 128/260; 424/78
[58] Field of Search ..................... 424/78, 22; 128/260

[56] References Cited

U.S. PATENT DOCUMENTS

| | | | |
|---|---|---|---|
| 2,720,502 | 10/1955 | Caldwell | 260/75 |
| 2,720,504 | 10/1955 | Caldwell et al. | 260/75 |
| 3,280,077 | 10/1966 | Case et al. | 260/75 |
| 3,755,558 | 8/1973 | Scribner | 424/47 |
| 3,773,919 | 11/1973 | Boswell et al. | 424/19 |
| 4,010,196 | 3/1977 | Tsuk | 260/484 A |

FOREIGN PATENT DOCUMENTS 835,442   5/1960   United Kingdom.

OTHER PUBLICATIONS

"Polyesters of Diglycollic Acid," Korshak et al., Akademy of Sciences, USSR, Bulletin: Div. Chem. Sci. 1957, 889–893.

"Polyethylene Terephthalate Fiber," Petakhov et al., Chemical Abstracts 56, 13119f (1962).

*Primary Examiner*—Harold D. Anderson
*Assistant Examiner*—E. A. Nielsen
*Attorney, Agent, or Firm*—Charles F. Costello, Jr.

[57] ABSTRACT

A normally solid biodegradable hydrolyzable polyester resin of diglycolic acid and an unhindered glycol having a molecular weight sufficiently high so as to provide a polymeric material possessing self-supporting film forming properties and the process of preparing the same and the use of the polymeric material as a device for the controlled continuous administration of a predetermined dosage of a drug to a living animal.

4 Claims, No Drawings

HIGH MOLECULAR WEIGHT POLYESTER RESIN, THE METHOD OF MAKING THE SAME AND THE USE THEREOF AS A PHARMACEUTICAL COMPOSITION

This is a division of application Ser. No. 582,001, filed May 29, 1975, which in turn was a Division of application Ser. No. 418,138, filed Nov. 21, 1973, now abandoned.

BACKGROUND OF THE INVENTION

Polyester resins have been prepared in the past by reacting such carboxylic acids as diglycolic acid with a dihydric alcohol such as a glycol but these polyester resins of the prior art were of comparatively low molecular weight such as about 3,000 or 4,000 molecular weight and had an inherent viscosity of about 0.25. These low molecular weight polyesters of diglycolic acid and glycols were not capable of forming a self-supporting film and were suggested for use as a propellant plasticizer among other things. If one could produce a polyester of diglycolic acid and a glycol of sufficiently high molecular weight so as to provide a polymeric material which possesses self-supporting film forming properties, a film could be produced therefrom which films could provide a delivery system for a predetermined dosage of a drug by controlled continuous administration. Such a film would be a biodegradable film which would be hydrolyzable and which could be implanted or otherwise deposited in the body of a living animal which would release the dosage of a drug and when the function as a dosage release device had served its purpose the hydrolyzable biodegradable film would be substantially completely absorbed in varying periods of time.

FIELD OF THE INVENTION

The present invention is in the field of polyester resins and more particularly of normally solid biodegradable polyester resins prepared by reacting diglycolic acid with an unhindered glycol to form a high molecular weight material which has a sufficiently high molecular weight so as to provide a polymeric material possession self-supporting film forming properties. The concept of the present invention is also in the field of devices useful for controlled continuous administration of a predetermined dosage of a drug to a living animal in which said polyester resin is used as the vehicle or carrier

DESCRIPTION OF THE PRIOR ART

The instant applicants are aware of the literature publication "Isvest. Akad. Nauk S.S. S.R., Otdel. Khim. Nauk, 1957 863–5 cf. CA 50 5529i, ibid 866–70." This reference describes diglycolic acid glycol polyesters having a molecular weight in the order of magnitude of about 3450. The U.S. Pat. Nos. 2,942,964 and 2,946,671 describe ethylene glycol diglycolate having a molecular weight in the order of magnitude of 300–400 and are suggested as being useful as a propellant plasticizer.

SUMMARY OF THE INVENTION

This invention relates to a normally solid biodegradable polyester resin prepared by esterifying diglycolic acid with an unhindered glycol so as to provide a polymeric material having a molecular weight sufficiently high so as to possess self-supporting film forming properties. The invention also relates to a process for preparing a polyester resin comprising heating at a temperature between about 125° C and 250° C. under a blanket of an inert gas such as nitrogen, diglycolic acid and an unhindered glycol in the presence of from about 0.01% and 0.5%, by weight, based on the weight of the diglycolic acid of antimony trioxide until a polyester is produced having a molecular weight sufficiently high so as to provide a polymeric material possessing self-supporting film forming properties. This invention also relates to the use of such a high molecular weight polyester resin in the form of a device for the controlled continuous administration of a predetermined dosage of a drug to a living animal. In such a device, the drug is dispersed throughout the device from a selected drug formulation.

Among the glycols which may be used to esterify the diglycolic acid in keeping with the concept of the present invention are ethylene glycol, diethylene glycol, 1,2-propylene glycol, 1,3-propylene glycol, 1,4-butylene glycol, dipropylene glycol, 1,5-pentanediol, 1,6-hexanediol, 1,7-heptanediol, 1,8-octanediol and the like. These and other glycols may be used individually or in combination with one another. These glycols when reacted with the diglycolic acid should be used in molar amounts substantially equivalent to the dicarboxylic acid although in order to achieve substantially full esterification it is frequently desirable to use an excess of the glycol components in an amount of about 10 to 150 mole percent over and beyond the stoichiometrically calculated amount necessary to esterify all of the carboxyl groups of the diglycolic acid. As the molecular weight of the polyester increases during the esterification reaction, excess glycol is removed. When the esterification reaction is completed, the excess glycol, if any, can be removed.

If it is desired to make a cross-linkable diglycolic acid polyester, one can incorporate into the reaction mass relatively small amounts of an $\alpha,\beta$-ethylenically unsaturated dicarboxylic acid such as maleic acid, fumaric acid, citraconic acid, itaconic acid, chloromaleic acid, and the like. Wherever available the anhydrides of these acids may also be used. These $\alpha,\beta$-ethylenically unsaturated dicarboxylic acids may be used either singly or in combination with one another in the diglycolic acid polyester. The amount of these dicarboxylic acids used with the diglycolic acid may be present in amounts sufficient to provide a reacted content of up to about 25 mole percent and preferably 10 mole percent of the $\alpha,\beta$-ethylenically unsaturated dicarboxylic acid wherein said mole percentages are based on the total moles of all of the dicarboxylic acids present.

In practicing the process of the present invention one can utilize as the catalytic material antimony trioxide in an amount varying between about 0.1% and 0.5%, by weight, based on the weight of the diglycolic acid. It is preferred to use between about 0.05% and 0.25%, by weight, of the antimony trioxide, based on the weight of diglycolic acid. The esterification reaction may be carried out at a temperature between about 125° C. and 250° C and preferably between about 150° C. and 225° C. In order to achieve the high molecular weight polyester of the present invention, the esterification reaction is carried out in three steps. The temperature ranges set forth hereinabove are applicable to all three steps. In the first step the heating can be carried out over a period of about 1 to 5 hours at about 175° C. under an atmosphere of an inert gas such as nitrogen or carbon dioxide. In this first step, atmospheric pressure is generally used. In the second step, the pressure in the system is reduced to about 1.5 mm. of mercury and the heating is carried out for a period of from about 8 hours to about 24 hours. Ordinarily the temperature would be about 175° C. In the third step, a higher vacuum (lower pressure) is applied in the order of magnitude of about 0.4 mm. of mercury and the period of time is generally between about 2 hours and 36 hours until a very viscous melt is produced. In the first step it is preferred to continue the heating for a period varying between about 2 hours and 3½ hours. In the second step it is preferred to use the heating time of between about 15 hours and 18 hours and in the third step it is preferred to use a heating time of between about 6 hours and 24 hours. The temperature selected will vary inversely with time, i.e. the higher the temperature, the shorter time interval and vice-versa.

In order that the concept of the present invention may be more completely understood, the following examples are set forth in which all parts are parts by weight unless otherwise indicated. These examples are set forth primarily for purposes of illustration and any specific enumeration of detail contained therein should not be interpreted as a limitation of this application except as is indicted in the appended claims.

EXAMPLE 1

Into a suitable polymerization reactor, fitted with a T-tube so that a capillary bubbler could be inserted through one port and the volatiles removed through the other port, there was introduced a blend of 26.8 parts of diglycolic acid (0.20 mol)(recrystallized from water using decolorizing charcoal) and 0.040 part of antimony trioxide. The blend of these two components was rinsed into the polymerization vessel with 24.8 parts of ethylene glycol (0.40 mol) that had been purified by treatment with sodium under nitrogen followed by distillation. A capillary bubbler was inserted into the polymerization reactor through a rubber seal so that the bottom of the bubbler was above the liquid in the reaction vessel. The system was purged with argon and then was immersed in a fluidized bed sand bath heated to 175° C. The vessel was adjusted until the sand was just above the level of the reactants, and then the capillary tube was pushed to the bottom of the liquid. The volatiles were distilled out of the reactor through the side port and collected in a trap. After 2¾ hours at 175° C. the pressure was gradually reduced so that after 45 minutes the pressure had reached 1.5 mm. of mercury. The reaction was continued for 16½ hours under these conditions. Thereupon the reaction vessel was immersed up to its neck, and the pressure was further reduced to about 0.4 mm. of mercury. After 8½ hours under these conditions, the reaction was discontinued. The product produced was a dark brown, clear, rubbery material having an inherent viscosity in hexafluoro-acetone sesquihydrate of 0.78 (0.5% conc., 30° C). The polymer was also soluble in chloroform. Analysis: Calculated for $C_6H_8O_5$:C,45.00; H,5.04; Found: C,44.61; H,5.04.

EXAMPLE 2

Into a suitable polymerization vessel equipped as in Example 1, there was introduced a mixture of 26.8 parts (0.20 mol) of diglycolic acid, 0.040 part of antimony trioxide and 30 parts of 1,3-propylene glycol (0.40 mol) which had been distilled under vacuum. The system was purged with argon and the mixture was heated for 2 hours at 175° C. whereupon the pressure was reduced over a 25 minute period to 1 mm. The reaction was continued for 15½ hours under these conditions. The tube was then inserted in the bath as far as possible and the pressure was further reduced to 0.4–0.5 mm. Heating was continued at about 175° C. under these reduced pressure conditions for an additional 24½ hours to produce a very viscous, amber product. After cooling the reaction mixture, 24.2 parts of a tough, flexible, and opaque polymer was recovered. This material had an inherent viscosity of 0.85 in hexafluoroacetone sesquihydrate (0.5% conc., 30° C.) Analysis: Calculated for $C_7H_{10}O_5$: C,48.27; H,5.79; Found: C,48.18, 47.71; H,5.52,5.77.

EXAMPLE 3

The procedure of Example 1 was followed again but in this case 13.4 parts (0.10 mol) of diglycolic acid, 0.020 part of antimony trioxide and 16.7 parts of 1,2-propanediol (0.22 mol, treated with sodium under argon and distilled) were introduced into the polymerization reaction vessel. After 3 hours at 175° C. and atmospheric pressure under a blanket of argon gas, the pressure was gradually reduced and the reaction was continued for an additional 24 hours at 0.3 mm. of mercury with the argon slowly bubbled through the reaction mixture. The product was an amber, rubbery and transparent material with an inherent viscosity of 0.68 in hexafluoroacetone sesquihydrate (0.5% conc., 30° C.). Analysis: Calculated for $C_7H_{10}O_5$: C,48.27; H,5.79; Found: C,48.15; H,5.75.

EXAMPLE 4

The procedure of Example 1 was followed again except that there was introduced into the polymerization vessel 25.20 parts of diglycolic acid (0.188 mol), 1.40 parts of fumaric acid (0.012 mol) and 0.040 part of antimony trioxide followed by the addition of 30 parts of 1,2-propanediol (0.40 mol). The charge was heated at 175° C. for 2½ hours under a blanket of argon gas. The pressure was then reduced over a 20–30 minute period to about 1 mm. of mercury and the reaction was continued at 175° C. for 16 hours. The reaction vessel was immersed as far as practicable in the sand bath and the pressure was further reduced to 0.4–0.5 mm. of mercury. Heating was continued under these conditions for a final 15 hours. The product thus produced was light amber, clear and rubbery and had an inherent viscosity of 0.42 in hexafluoroacetone sesquihydrate (0.5% conc., 30° C.). Analysis by nuclear magnetic resonance indicated 3.6 mole percent of the fumarate.

EXAMPLE 5

Example 4 was repeated in all essential details except that there was used 5 mole percent of fumaric acid. Analysis of the product by nuclear magnetic resonance indicated 4.2 mole percent of fumarate units.

EXAMPLE 6

Example 4 was repeated again in all essential details except that there was used 10 mole percent of fumaric acid. Nuclear magnetic resonance analysis indicated 7.3 mole percent of fumarate in the resulting polymer. The intrinsic viscosity of this product was 0.77 when measured on a 0.5% solids solution of the polymer in hexafluoroacetone sesquihydrate at 30° C.

EXAMPLE 7

The procedure of Example 1 was followed in all essential details except that there was used a mixture of 25.5 parts of diglycolic acid (0.190 mol), 1.16 parts of maleic acid (0.010 mol) and 0.040 part of antimony trioxide and 30 parts of 1,2-propanediol (0.40 mol). The initial heating period was 3 hours at 175° C. and atmospheric pressure under a blanket of nitrogen. The reaction mixture was then heated for 7½ hours at 0.3–0.5 mm. of mercury. The resulting product was a clear, reddish, rubbery semisolid which had an inherent viscosity of 0.40 (0.5% conc., 30° C.). Nuclear magnetic resonance analysis showed that the maleic acid had been largely isomerized to form fumarate esters. The total unsaturated acid moiety present was about 2.6 mole percent and the ratio of fumarate to maleate was about 4.5:1.

EXAMPLE 8

The procedure of Example 1 was followed in all essential details except that the side port was heated to facilitate the removal of the butanediol used in this example. Into the reaction vessel there was introduced 26.8 parts of diglycolic acid (0.20 mol), 0.040 part of antimony trioxide and 36.0 parts of 1,4-butanediol (0.40 mol, redistilled). The charge was heated under a nitrogen purge for 2 hours at 175° C. before the pressure was gradually reduced to 0.8 mm. of mercury. The reaction was permitted to continue at 175° C. and 0.5–0.8 mm. for 23½ hours. During the last 7½ hours, the polymerization vessel was immersed up to its neck in the 175° C. bath. At the end of the reaction the polymerization mixture was allowed to cool to room temperature under a nitrogen atmosphere. Further cooling in liquid nitrogen freed most of the polymer amounting to 36.5 parts (theoretically 37.6 parts) from the glass container; some additional polymer adhered strongly to the glass container and was not recovered. The polymer thus recovered was dissolved in chloroform and the solution was filtered. After the filtered solution was diluted sevenfold with acetone, the precipitated polymer was recovered by filtration, washed with acetone and dried to a constant weight at 40°–45° C. under reduced pressure. The polymer had an inherent viscosity of 0.65 (0.5% concentration in chloroform at 30° C.) and a melting point of 77° C. (differential thermal analysis). Analysis: Calculated for $C_8H_{12}O_5$:C,51.06; H,6.43; Found C51.03; H,6.17.

EXAMPLE 9

In this example the reaction vessel used in Example 1 was modified with a heated wide-bore side-arm tube so that the exit port would not become plugged with excess diol. There was introduced into this modified reaction vessel a mixture composed of 16.8 parts of diglycolic acid, (0.125 mol), 29.5 parts of hexamethylene glycol, (0.25 mol) and 0.025 part of antimony trioxide. After the reaction mixture had been heated for 2 hours at 175° C. the pressure was gradually reduced to 0.8 mm. of mercury and the polymerization vessel was slowly lowered into the sand bath so as to maintain a steady evolution of excess diol. After the bulk of the excess diol had been removed, the pressure was reduced further to 0.2–0.3 mm. and the reaction was continued until a very viscous melt was achieved. The resulting cloudy, tough, amber polymer had an inherent viscosity of 0.70 in chloroform (0.5% conc., 30° C.). Re-precipitation of this material was effected by cooling an acetone solution of the polymer to −78° C. and then removing the acetone under reduced pressure at −50° - 60° C. The caked residue was further dried under reduced pressure at room temperature. Analysis: Calculated for $C_{10}H_{16}O_5$:C,55.54; H,7.46; Found: C,54.97; H,7.43.

EXAMPLE 10

A solution of the polymer prepared according to Example 3, namely the polyester of 1,2-propylene glycol and diglycolic acid, was prepared by dissolving 0.9 part of said polymer and 0.045 part of benzophenone in 3 vols. of hexafluoroacetone sesquihydrate. A film was cast from this solution, air-dried, and irradiated for 12 hours with a Hanovia 100 watt ultraviolet lamp at a distance of 3.25 inches. After irradiation, the tough, self-supporting film became highly swollen in hexafluoroacetone sesquihydrate but did not redissolve.

EXAMPLE 11

The polymer prepared according to Example 4 (1 part) was dissolved in 1.5 vols. of acetone together with 0.010 part of benzoyl peroxide. A film cast from this solution was air-dried and cured for 1 hour at 100° C. in a vacuum oven. The cured film became highly swollen in chloroform but did not dissolve, whereas the uncrosslinked polymer is soluble in chloroform.

EXAMPLE 12

Example 11 is repeated in essential details except that there is added to the solution 0.05 part of ethylene glycol dimethacrylate. A film was also cast from this solution, air-dried and cured for about 1 hour at 100° C. in a vacuum oven. The film became highly swollen in chloroform but did not dissolve although, as in Example 11, it was noted that the uncross-linked polymer was soluble in chloroform.

The polyester resins of the present invention can be used to manufacture a device for the controlled continuous administration of a predetermined dosage of a drug.

The biodegradable polymeric compositions of the present invention are particularly useful in formulating pharmaceutical compositions. Illustrative of such pharmacologically active compounds which can be employed include the following: nitroglycerine, anti-viral agents, triamcinolone acetonide, enzymes i.e. streptokinase, papain, aspariginase etc., nitroimidazole, nitrofurdantoin, 17α-ethynyl-17β:hydroxy-5(10)-estren-3-one, α-cyclohexyl-α-phenyl-1-pipiridine-propanol hydrochloride, pilocarpine, acetazolamide, prostaglandins, diethylcarbamazine.

For a specific example, dosage rates for the biologically active compounds recited herein are not given. However, such materials are well known and dosage rates are established for them in different applications. By application of this knowledge, those skilled in the art can formulate controlled release biologically or otherwise active composition in accordance with this invention.

Medicine, medication or other biologically active compositions including drugs may be incorporated into a device comprising the polydiglycolic acid esters of the present invention by various techniques such a by solution methods, suspension methods or melt pressing.

For instance, 52 mg. of pilocarpine hydrochloride was dissolved in 95% ethyl alcohol (0.5 ml.) and 0.5 ml.

of said solution was added to a solution of poly-(1,4-butylenediglycolate)(0.95 g. polymer dissolved in 3 ml. of chloroform). The resulting solution was cast into a film and after drying in air and then under vacuum, the film was hazy, strong and cold drawable.

As an alternative approach, finely ground pilocarpine hydrochloride (50 mg.) was added to a solution of the polymer, as in the preceding method, except that the hydrochloride was in suspension. The mixture was agitated until a good dispersion was obtained and the dispersion was then cast into a film and dried as before.

The film from the solution method set forth hereinabove was cut into large pieces and put between aluminum foils separated by 6 mil shims. The "sandwich" was pressed between chrome plated steel plates at a platen temperature of about 100° C. for 30 seconds after preheating for 3 minutes. The sandwich was allowed to stand over night in a desiccator to give the polymer time to crystallize.

Various other delivery devices may be manufactured from these polyester compositions to administer drugs via a number of routes. For example, an intrauterine device for releasing an anti-fertility agent at a controlled rate for prolonged period of time; a medical bandage for use in the continuous administration of controlled quantities of systemically active drugs over a prolonged period of time by absorption through the external body skin or mucosa; a strip which could be inserted between the gum and the cheek so that absorption of the medicament at a predetermined interval through the buccal mucosa into the bloodstream may take effect. Drugs could also be incorporated into fine particles of these polyester resins and subsequently a dispersion of these particles could be injected parenterally, subcutaneously, intramuscularly etc., at which site the polymer would slowly biodegrade and release the drug over a prolonged period of time. Other methods of drug administration can be envisaged and those skilled in the art can manufacture controlled release devices from these compositions in accordance with the present invention.

An effective continuous dosage rate for pilocarpine hydrochloride therapy of glaucoma is approximately 20 μg per hour and a predetermined amount could be incorporated into a device such as a pledget of the polyesters of the present invention in the form of a thin circular disc. It is believed that the pledget biodegrades at the surface only, thereby gradually eroding and simultaneously releasing the drug so that the area of release remains substantially constant during degradation. A simple expression can be derived which relates the area, thickness, drug concentration, density and the dosage rate to the life expectancy of the pledget, i.e., the time required to biodegrade completely. This simple expression is as follows:

$$t = (L A C \delta / 48 d)$$

where
$t$ = Pledget lifetime in days
$L$ = Pledget thickness in microns
$A$ = Pledget area in cm$^2$
$C$ = Drug concentration, % by volume
$\delta$ = Density of the drug, g/cc
$d$ = Delivery rate, μg/hour Lifetime/concentration values were calculated for a model pledget with a total surface area of 1.5 cm$^2$ and a thickness of 1mm, delivering a drug with unit density at a rate of 20 μg per hours.

| Lifetime | Drug Concentration, % by Volume |
|---|---|
| 1 day | .64 |
| 1 week | 4.48 |
| 7.8 days | 5.0 |
| 1 month (30 days) | 19.2 |
| 3 months | 57.6 |

Thus, depending on the biodegradation time of the polymer, it should be possible to obtain reasonable dosages by varying the drug concentration in a practical range.

Certain of the polyesters of the present invention will have elastomeric characteristics whereas other polyesters of the present invention, with higher melting points and some measure of crystallinity, may be formed into filaments which display excellent tensile strength and thereby are usable individually or collectively, such as in braided form, as a sterile suture or ligature. Additionally these diglycolate polyester materials of the present invention may be used as a coating material on sutures and ligatures whether as individual fibers or braided structures. For instance, the poly(1,4-butylene diglycolate) prepared according to Example 8 having a melting point in the vicinity of 77° C. would be suitable for use in making a suture fiber because this polymeric material is a crystalline polymer and for this purpose it is desired that the polymeric material have at least a certain measure of crystallinity. When the polyesters of the present invention are to be used as a braid coating to improve the knot run-down characteristics of a suture or ligature, the polymeric material is dissolved in a suitable solvent such as chloroform and the filament and braided structure is coated with the solution of the polymer by dipping, brushing spraying and the like and the solvent is then evaporated, thereby depositing a film of the polymer on the filaments or the braid. The lower melting polymers of the present invention are particularly good for coating the ligatures and sutures in order to impart the desired degree of slipperiness thereto. These coatings can be applied to the polyglycolic acid sutures and ligatures as disclosed in the U.S. Pat. No. 3,297,033 which patent is incorporated herein by reference. Other suture material such as those made from polyethyleneterephthalate may also be coated with films of the polymers of the present invention.

The following example shows a method for coating braided polyglycolic acid filaments with diglycolate polyesters.

EXAMPLE 13

Polyglycolic acid filamentary braid was dip coated with the poly(ethylene diglycolate) of Example 1 by passing the braid through either a 1%, 2% or 4% (wt./vol.) solution of the diglycolate in chloroform. The wet braid was dried at room temperature to volatilize the solvent and leave a 0.93% to 4.6%, by weigh, coating (based on the weight of the braid) of the poly(ethylene diglycolate) deposited on the braid surface. Other poly(alkylene diglycolates) and diglycolate copolymers were coated onto PGA braid in a similar manner.

Comparative knot run-down tests were made with the poly(alkylene diglycolate) coated braid, beeswax coated braid, and an uncoated polyglycolic acid control. These evaluations were carried out by looping the braid around a rigid rod, casting a knot in the upper part of the braid and subjectively estimating the relative ease with which the knot could be slipped down the length of the braid and tightened around the rod. In these tests, an improvement in slip approximately equivalent to beeswax was noted for poly[1,2-propylene diglycolate fumarate maleate], poly[1,2-propylene diglycolate fumarate], poly[1,3-propylene diglycolate], and poly[ethylene diglycolate], In addition to using the polyesters of diglycolic acid of the present invention as devices for the controlled continuous administration of a predetermined dosage of a drug and the use in making filaments for sutures and ligatures in a sterile state, and the use of the polydiglycolic acid esters as a coating for braided sutures and ligatures, one could use the polyesters of diglycolic acid to make solid products by molding or machining so as to produce orthopedic pins, clamps and the like, or fibrillar products made from filaments of the polydiglycolic acid esters can be knitted or woven for use as burn dressings, gauze bandages and the like. Other comparable uses could be adapted for other medical purposes such as those disclosed in the U.S. Pat. No. 3,739,773, which patent is incorporated herein by reference.

We claim:

1. A pharmaceutical composition for the controlled continuous administration of a predetermined dosage of a drug to a living animal comprising a normally solid biodegradable, hydrolyzable polyester resin of diglycolic acid and an unhindered glycol, having a molecular weight sufficiently high so as to provide a polymeric material possessing self-supporting film forming properties, which has dispersed uniformly throughout said polyester resin, a drug formulation.

2. A pharmaceutical composition according to claim 1 in which the polyester resin contains a reacted content of up to 25 mole percent of at least one $\alpha,\beta$-ethylenically unsaturated dicarboxylic acid based on the total moles of all of the dicarboxylic acids present.

3. A pharmaceutical composition according to claim 1 in the form of a self-supporting film.

4. A pharmaceutical composition according to claim 1 in which the polyester resin contains a reacted content of up to 10 mole percent of at least one $\alpha,\beta$-ethylenically unsaturated dicarboxylic acid based on the total moles of all of the dicarboxylic acids present.

* * * * *